United States Patent [19]

Gauthier et al.

[11] 4,254,121

[45] Mar. 3, 1981

[54] 3-OXO-5H-PYRIMIDO[2,1-c][1,4] BENZOXAZINES

[75] Inventors: Jean A. Gauthier; Ivo L. Jirkovsky, both of Montreal, Canada

[73] Assignee: Ayerst, McKenna & Harrison Inc., Montreal, Canada

[21] Appl. No.: 65,789

[22] Filed: Aug. 13, 1979

[51] Int. Cl.³ .................... A61K 31/535; C07D 498/14
[52] U.S. Cl. .......................... 424/248.55; 424/248.57; 544/101
[58] Field of Search .................... 544/101; 424/248.57, 424/248.55

[56] References Cited

U.S. PATENT DOCUMENTS

| | | | |
|---|---|---|---|
| 3,696,095 | 10/1972 | Hellerbach et al. | 424/248.57 |
| 4,017,625 | 4/1977 | Kadin | 424/251 |
| 4,031,217 | 6/1977 | Kadin | 424/251 |
| 4,066,766 | 1/1978 | Kadin | 424/251 |
| 4,134,974 | 1/1979 | Melloni et al. | 424/248.54 |
| 4,145,419 | 3/1979 | Rowlands et al. | 544/101 |

OTHER PUBLICATIONS

Stoss, P., Chem. Ber., 111(1), 314–319 (1978).

*Primary Examiner*—Ethel G. Love
*Attorney, Agent, or Firm*—Arthur E. Wilfond

[57] ABSTRACT

3-Oxo-5H-pyrimido[2,1-c][1,4]benzoxazine derivatives, optionally substituted with a hydroxymethyl, carboxy or lower alkoxycarbonyl at position 1 and optionally substituted at positions 8 or 9, with a lower alkyl or halo are disclosed. The derivatives are antiallergy agents and methods for their preparation and use are given.

12 Claims, No Drawings

3-OXO-5H-PYRIMIDO[2,1-c][1,4]BENZOXAZINES

BACKGROUND OF THE INVENTION (a) Field of the Invention

This invention concerns a class of pyrimido [2,1-c][1,4]benzoxazine derivatives. More specifically, this invention relates to 3-oxo-5H-pyrimido [2,1-c][1,4]benzoxazine derivatives, to a process for their preparation, to pharmaceutical formulations thereof and to methods for using the derivatives. The derivatives are useful for treating anaphylactic reactions and allergic conditions in mammals.

(b) Description of the Prior Art

A search of the chemical literature indicates that the compounds of this invention represent a novel tricyclic ring system. A number of related tricyclic compounds are described in the following reports: S. B. Kadin, U.S. Pat. No. 4,017,625, issued May 24, 1976; S. B. Kadin, U.S. Pat. No. 4,066,766, issued Jan. 3, 1978, S. B. Kadin and P. F. Moore, U.S. Pat. No. 4,031,217, issued June 21, 1977. These references disclose compounds which, like the compounds of this invention, are tricyclic; however, the tricyclic compounds in these references differ by being "carba" analogs.

SUMMARY OF THE INVENTION

The compounds of this invention are represented by formula I

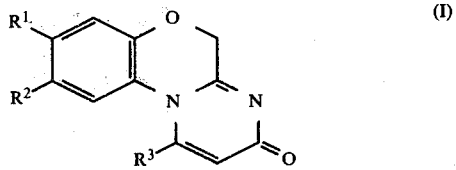

in which $R^1$ and $R^2$ are the same or different selected from the group of hydrogen, lower alkyl and halo; and $R^3$ is hydrogen, hydroxymethyl or lower alkoxycarbonyl.

A group of preferred compounds of formula I are those having at least one of the following features: $R^1$ is hydrogen or methyl; $R^2$ is hydrogen, tert-butyl or chloro; and $R^3$ is hydrogen, hydroxymethyl or ethoxycarbonyl. Of these, compounds having all the preceding features particularly are preferred.

A more preferred group of compounds of formula I are those wherein: $R^1$ is hydrogen or methyl; $R^2$ is hydrogen or chloro; and $R^3$ is ethoxycarbonyl.

The compounds of formula I are prepared by a method described herein.

A method is provided for preventing or treating anaphylactic reactions or allergic conditions in a mammal which comprises administering to said mammal an effective anaphylactic alleviating or allergic alleviating amount of the compound of formula I.

A pharmaceutical formulation also is provided comprising the compound of formula I as an active ingrediant together with a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, t-butyl, pentyl, hexyl and the like. 1,1-Dimethylethyl as used herein is also known as tert-butyl.

The term "halo" as used herein means halogens and includes fluorine, chlorine, bromine and iodine, unless stated otherwise.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkanol" as used herein means both straight and branched chain alkanols containing from one to four carbon atoms and includes methanol, ethanol, isopropanol, butanol and the like.

ANTI-ALLERGIC ACTIVITY

The compounds of this invention of formula I are useful in the prevention or treatment of allergic reactions in a mammal.

More specifically, the compounds of this invention are useful for the prophylactic treatment as well as for the management of anaphylactic reactions and atopic allergic manifestations, for example, bronchial asthma, hay fever, allergic rhinitis, allergic conjunctivitis, food allergies, urticaria and the like, in a sensitized mammal.

The prevention or treatment of allergic reactions in a mammal by administration of a compound of formula I is demonstrated by using known anti-allergic tests in an appropriate animal model. An example of such a test is the passive paw anaphylaxis (PPA) method, described by R. R. Martel and J. Klicius, Int. Archs. Allergy Appl. Immun., 54, 205 (1977). In this method reaginic antibody-induced hypersenstivity is produced in the rat hindpaw. Increased vascular permeability is determined by measuring the increase in paw volume. An effective anti-allergic drug inhibits the increase in paw volume when compared to untreated reaginic hypersensitive controls. For example, according to this test: 3-oxo-5H-pyrimido [2,1-c][1,4]benzoxazine-1-carboxylic acid, ethyl ester (described in Example 4) at an intraperitoneal dose of 10 mg/kg of body weight causes a 40% inhibition of the increase in paw volume, at 15 minutes; 9-chloro- 3-oxo-5H-pyrimido-[2,1-c][1,4]benzothiazine-1-carboxylic acid, ethyl ester (described in Example 4) at an intraperitoneal does of 30 mg per kg of body weight causes a 48% inhibition of the increase in paw volume at 15 minutes; and 9-chloro-5H-pyrimido[2,1-c][1,4]benzoxazin-3-one (described in Example 6) at an intraperitoneal dose of 30 mg per kg of body weight causes a 19% inhibition of the increase in paw volume at 15 minutes.

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administratin and standard biological practice.

For example, they are administered orally in solid form i.e. capsule or tablet. They can also be administered orally in the form of suspensions or solutions or they may be injected parenterally. They can be administered parenterally by the nasal route, for instance, as drops or aerosol; or by inhalation from an aerosol.

In addition, the compounds of this invention can be administered in conjunction with common anti-allergic agents, for example, known compounds effecting antihistaminic, analgesic, central nervous system depressant, anti-hypertensive, immunosupressive, anti-bradykinin, anti-serotonin or endocrinological responses.

The tablet compositions for oral administration contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I for oral administration contain the active ingredient the admixture with one or more non-toxic pharmaceutical excipients known to be suitable in the manufacture of aqueous suspension. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions for oral administration can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or ethyl alcohol. These compositions can also contain a sweetening agent, flavoring agent and antioxidant.

For administration to a mammal by parenteral injection, it is preferred to use the compounds of formula I in solution in a sterile aqueous vehicle which may also contain other solutes, such as buffers or preservatives, as well as sufficient quantities of pharmaceutically acceptable salts or of glucose to make the solution isotonic.

The compounds of formula I can also be administered as nasal powders or insufflations. For such purpose the compounds are administered in finely divided solid form together with a pharmaceutically acceptable solid carrier, for example, a finely divided polyethylene glycol (e.g. "Carbowax 1540") or finely divided lactose. Such compositions may also contain other excipients in finely divided solid form.

For administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of formula I as antiallergic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, an effective anti-allergic amount of a compound of formula I usually ranges from about 0.1 mg to about 500 mg per kg of body weight per day in single or divided dose, although as aforementioned, variations will occur. However, a dosage level that is in the range from about 0.5 mg to about 200 mg per kg of body weight per day in single or divided dose is employed most desirably in order to achieve effective results.

PROCESS

For the preparation of the compounds of formula I, the preferred starting materials are the compounds of formula II in which $R^1$ and $R^2$ are the same or different selected from the group or hydrogen, lower alkyl and halo. Reaction Scheme I illustrates a preferred method for the preparation of the starting materials of formula II.

REACTION SCHEME I

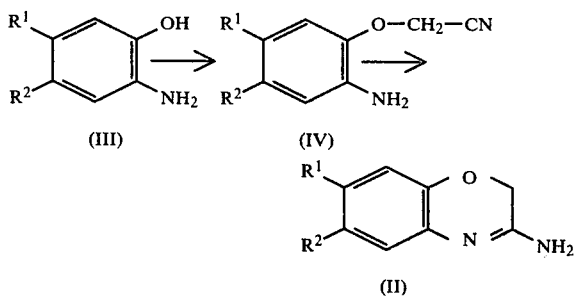

(III) (IV)

(II)

The sequence of reactions illustrated in Reaction Scheme I essentially is described by M. Mazharuddin and G. Thyagarajan, Chem. Ind. (London), 178 (1971) for the preparation of the compound of formula II in which $R^1$ and $R^2$ are hydrogen. For the preparation of the compounds of formula II, the phenol derivatives of formula III either are known and commercially available or are prepared by conventional methods described in the chemical literature. Condensation of the compound of formula III in which $R^1$ and $R^2$ are the same or different selected from the group of hydrogen, lower alkyl and halo with 1.1 to 1.5 molar equivalents of chloroacetonitrile and potassium carbonate in acetone at 20° to 60° C. for four to ten days affords the corresponding compound of formula IV in which $R^1$ and $R^2$ are as defined immediately above. In turn, the compound of formula IV is treated with five to eight molar equivalents of sodium methoxide in methanol at 15° to 30° C. for one-half to five hours to give the corresponding compound of formula II in which $R^1$ and $R^2$ are as defined immediately above.

The compound of formula II in which $R^1$ and $R^2$ are the same or different selected from the group of hydrogen, lower alkyl and halo is in turn reacted with at least one, preferably 1.0 to 1.2 molar equivalents, of a compound of formula $R^3C \equiv C-COO-$(lower alkyl) in which $R^3$ is hydrogen, hydroxymethyl or lower alkoxycarbonyl to obtain the corresponding compound of formula I in which $R^1$, $R^2$ and $R^3$ are as defined herein. The reaction is performed conveniently in an organic solvent at temperatures from 10° to 100° C., preferably 40° to 80° C. Suitable organic solvents include the lower alkanols, for instance methanol or ethanol, tetrahydrofuran, benzene and dioxane. The time required for the reaction depends on the reaction temperature, with times of one hour to two days usually being sufficient.

The following examples illustrate further this invention.

EXAMPLE 1

2-Amino-4-(1,1-dimethylethyl)phenol [III; $R^1=H$ and $R^2=C(CH_3)_3$]

4-(1,1-Dimethylethyl)phenol (30.0 g, 200 mmol) was added to a vigorously stirred solution of sodium hydroxide (24.5 g, 500 mmol) in water (540 ml). The mixture was heated over a steambath to dissolve the phenol. The solution was cooled to 10° C. Benzenediazonium chloride [prepared from aniline (18.6 g, 200 mmol), crushed ice (250 g), concentrated hydrochloric acid (58 ml) and sodium nitrite (14.3 g, 200 mmol)] was added to the stirred suspension. After the addition (40 min), the precipitate was collected and air dried to afford the azo derivative as an orange powder (49.3 g), mp 65–66° C.

A part of this latter material (48.0 g, 189 mmol) was suspended in aqueous sodium hydroxide (69.5 g in 400 ml of water). The suspension was heated at 75° C. while sodium dithionite (87 g) was added in portions over a period of 1 hr. At the end of the addition, the red color changed to a straw like tint. The hot solution was mixed with charcoal and filtered through a cake of diatomaceous earth. The solution was rendered acidic with aqueous 6N hydrochloric acid to pH 5–6. Upon cooling a tan precipitate was deposited in the solution. The precipitate was collected and air-dried to give the title compound as a tan powder (19.3 g); mp 158–159° C.; NMR(DMSO-$d_6$) δ 1.25 (S, 9H), 4.25 (s, 2H), 6.5 (m, 3H), 8.0 (s, 1H).

EXAMPLE 2

2-Cyanomethoxy-5-(1,1-dimethylethyl)benzenamine [IV; $R^1=H$ and $R^2=C(CH_3)_3$]

2-Amino-4-(1,1dimethylethyl)phenol (90.0 g, 546 mol, described in Example 1) was dissolved in acetone (900 ml) and heated at reflux for 2 days in the presence of anhydrous potassium carbonate (81.0 g, 534 mmol) and chloroacetonitrile (40.5 g, 535 mmol). The mixture was allowed to stand for an additional day at 20°–24° C. The mixture then was treated with more potassium carbonate (15.0 g) and chloroacetonitrile (10 g) under the same conditions. The mixture was mixed with charcoal and filtered through diatomaceous earth. The filtrate was evaporated to afford a residue which, when dissolved in hexane containing a small amount of ethyl acetate, afforded tan crystals of the title compound; Anal. Calc'd for $C_{12}H_{16}N_2O$: C, 70.56%; H, 7.90%; N, 13.72%; Found: C, 70.60% H, 8.00%; N, 13.85%; IR(CHCl$_3$) 3460, 3380, 2240, 1620, 1515, 1166, cm$^{-1}$; NMR(CDCl$_3$) δ 1.3 (s, 9H), 3.7 (s,2H), 4.7 (s,2H), 6.75 (s, 3H).

In a similar manner, but replacing 2-amino-4-(1,1-dimethylethyl)-phenol with an equivalent amount of 2-aminophenol, 2-chlorophenol or 2-amino-5-methylphenol, the following compounds of formula IV were obtained, respectively: 2-cyanomethoxybenzenamine) described by M. Mazharuddin and G. Thyagarajan, cited above); mp 102° C.; IR(nujol) 3460, 3370, 2260 cm$^{-1}$; MNR(CDCl$_3$)δ3.85 (s, 2H) and 6.85 (m, 4H); 5-chloro-2-cyanomethoxybenzenamine; mp 68–70° C.; IR(CHCl$_3$) 3490, 3390, 1188 cm$^{-1}$; NMR(CDCl$_3$)δ3.9 (s,2H), 4.7 (s,2H), 6.7 (m, 3H); and 2-cyanomethoxy-4-methylbenzenamine; mp 87–89° C.; Anal. Calc'd for $C_9H_{10}N_2O$: C, 66.65%; H, 6.22%; N, 17.27%; Found: C, 66.90%; H, 6.13%; N, 18.06μ; IR(CHCl$_3$) 3450,3380 cm$^{-1}$; NMR(CDCl$_3$)δ2.25 (s,3H), 3.62 (s, 2H), 4.73 (s, 2H), 6.7 (m, 3H).

EXAMPLE 3

3-Amino-6-(1,1-dimethylethyl)-2H-1,4-benzoxazine [II; $R^1=R^2=C(CH_3)_3$]

2-Cyanomethoxy-5-(1,1-dimethylethyl)benzenamine (4.0 g, 19.6 mmol, described in Example 2) was dissolved in methanol (80 ml) containing 5.2 meq. of freshly prepared sodium methoxide. The mixture was stirred at 20° C. for 1 hr and evaporated. Water (100 ml) was added and the solution was extracted with methylene chloride. The organic extract was dried and evaporated, and the residue was crystallized from ethyl acetate-hexane to give the title compound (1.46 g, 37%); mp 155°–156° C.; Calc'd for $C_{12}H_{16}N_2O$:C, 70.56%; H, 7.90%; N, 13.72%; Found:C, 70.77%; H, 7.96%; N, 13.96%; (IR(CHCl$_3$) 3504, 3480, 3400, 1643, 1598, 1574 cm$^{-1}$; NMR(CDCl$_3$)δ1.32 (s,9H),4.43(s,2H), 6.60-7.10 (m,3H).

In a similar manner, but replacing 2-cyanomethoxy-5-(1,1-dimethylethyl)benzenamine with an equivalent amount of another compound of formula IV described in Example 2, the following compounds of formula II were obtained, respectively: 3-amino-2H-1,4-benzoxazine (described by M. Mazharudin and G. Thyagarajan, cited above); mp 117°–119° C.; NMR (CDCl$_3$)δ4.4(s,2H), 5.6 (s,2H),6.9(m,4H); 3-amino-7-methyl-2H-1,4-benzoxazine; mp 167°–170° C.; Anal. Calc'd for $C_9H_{10}N_2O$: C, 66.65%; H, 6.22%; N,17.27%; Found: C, 66.63%; H, 6.14%; N, 16.88%; IR(CHCl$_3$)3500, 3400, 3000, 1650 cm$^{-1}$; NMR(CDCl$_3$) δ2.3(s, 3H), 4.45 (s, 2H), 5.25(s, 2H), 6.8 (m, 3H); and 3-amino-6-chloro-2H-1,4-benzoxazine; mp 173°–175° C.; Anal. Calc'd for $C_8H_7ClN_2O$: C, 52.61%; H, 3.86%; N, 15.34%; Found: C, 52.56%, H, 3.85%; N, 14.86%; and NMR(CDCl$_3$) δ4.45 (s,2H), 6.85 (m,3H), 7.05 (s,2H).

EXAMPLE 4

3-Oxo-5H-pyrimido[2,1-c][1,4]benzoxazine-1-carboxylic Acid, Ethyl Ester (I, $R^1$ and $R^2=H$ and $R^3=COOEt$)

A solution of the compound of formula II, 3-amino-2H-1,4-benzoxazine(1.75 g, 11.08 mmol, described in Example 3) and diethyl acetylenedicarboxylate (2.2g, 12.9 mmol) dissolved in ethanol (30 ml) was stirred at room temperature for 2½ hours. The precipitate was collected to give 1.30 g of the title compound as colourless crystals; mp 174°–175° C. (after recrystallization from ethyl acetate-hexane); IR(CHCl$_3$) 1738, 1650 cm$^{-1}$; NMR(CDCl$_3$)δ1.2 (t, J=7Hz, 3H), 4.3(q,J=7Hz, 2H), 4.92 (s, 3H), 6.68 (s,1H), 7.3 (m,4H); M+272; Anal. Calc'd: C, 61.76%; H, 4.44%; N, 10.29%; Found: C, 61.99%; H, 4.35%; N, 10.32%.

The title compound was characterized further by reduction with sodium borohydride to give 4,4a-dihydro-3-oxo-5H-pyrimido[2,1-c][1,4] benzoxazine-1-carboxylic acid ethyl ester, mp 178°–179° C. (after recrystallization from ethyl acetate-hexane); IR (CHCl$_3$) 3400, 3180, 1600 cm$^{-1}$; NMR(CDCl$_3$)δ1.2 (t,J=7 Hz, 3H), 4.1 (m,4H), 5.14 (m1H), 5.9 (s,1H), 6.55 (m4H), 7.9

(s,1H); Anal. Calc'd: C, 61.31%; H, 5.5%; N, 10.21%; Found: C, 61.21%; H, 5.46%; N, 10.37%. Hydrolysis of the latter ester in the presence of potassium hydroxide gave the corresponding acid; mp>260° C. (after recrystallization from methanoldiethyl ether); IR(nujol) 2900, 1725, 1615$^{-1}$; NMR(DMSO-d$_6$)δ4.1 (m,J=6 Hz, J$_2^1$=4.5 Hz, 2H), 5.1 (m,J=6 Hz, J$_2^1$32 4.5 Hz, 1H), 5.85 (s,1H), 6.65 (m,4H), 8.05 (broad,1H). The aminoethanol addition salt of the latter acid has mp 154°–155° C. (after recrystallization from methanol-diethyl ether).

By following the procedure of Example 5, but replacing 3-amino-2H-1,4-benzoxazine with an equivalent amount of 3-amino-7-methyl-2H-1,4-benzoxazine, 3-amino-6-(1,1-dimethylethyl)-2H-1,4-benzoxazine, or 3-amino-6-chloro-2H-1,4-benzoxazine, each described in Example 3, there was obtained respectively:

8-methyl-3-oxo-5H-pyrimido[2,1-c][1,4] benzoxazine-1-carboxylic acid, ethyl ester: mp 156°–157° C.; IR(CHCl$_3$)1738, 1660 cm$^{-1}$;NMR(CDCl$_3$) δ1.3(t,J=7 Hz, 3H),2.4(s,3H),4.3(q,J=7 Hz),4.93(s,2H),6.8(m,4H); Anal. Calc'd: C, 62.93%; H, 4.93%; N, 9.79%; Found: C, 62.58%; H, 4.92%; N, 9.51%; 9-(1,1-dimethylethyl)-3-oxo-5H-pyrimido[2,1-c][1,4] benzoxazine-1-carboxylic acid, ethyl ester; IR(CHCl$_3$)1740, 1660, 1630cm$^{-1}$; NMR(CDCl$_3$)67 1.2 (t, J=7 Hz, 3H); 1.3(s,9H); 4.25(q,J=7HZ,2H), 4.86(s,2H);7.0(m,4H); and 9-chloro-3-oxo-5H-pyrimido[2,1-c][1,4] benzoxazine-1-carboxylic acid,ethyl ester; mp 136°–137° C.; IR(CHCl$_3$)1743, 1670, 1635 cm$^{-1}$; NMR (CDCl$_3$)δ1.3(t,J=7 Hz,3H); 4.46(q,J=7 Hz,2H);4.96(s,2H); 6.70(s,1H);7.00(m,1H);7.24 (m,2H); Anal. Calc'd: C, 54.82%; H, 36.90%; N, 9.14%; Found: C, 55.16%; H, 3.52%; N, 9.08%.

EXAMPLE 5

1-Hydroxymethyl-5H-pyrimido[2,1-c][1,4] benzoxazin-3-one(I; R$^1$and R$^2$=H and R$^3$=CH$_2$OH)

A solution of the compound of formula II, 3-amino-2H-1,4-benzoxazine (10.7 g, 72.1 mmol, described in Example 3) and hydroxymethylacetylenecarboxylate ethyl ester (9.7 g, 75.7 mmol) in ethanol (100 ml) was allowed to stand at room temperature (20° to 24° C.) for 6 days. The resulting precipitate was collected giving 12.03 g of the title compound as tan crystals with mp 235°-237° C., the mp remaining unchanged or recrystallization from ethanol. The title compound had IR(nujol) 3130, 1640 cm$^{-1}$; NMR(Trifluoroacetic acid)δ5.2 (s,2H); 5.3(s,2H); 7.6(m,5H); Anal. Calc'd: C, 62.60%; H, 4.38%; N, 12.17%; Found: C, 62.32%; H, 4.24%; N, 12.17%.

By following the procedure of Example 5, but replacing 3-amino-2H-1,4-benzoxazine with an equivalent amount of 3-amino-7-methyl-2H,-1,4-benzoxazine, 3-amino-6-(1,1-dimethylethyl)-2H-1,4-benzoxazine, or 3-amino-6chloro-2H-1,4-benzoxazine, each described in Example 3, there is obtained, respectively:

8-methyl-hydroxymethyl-5H-pyrimido[2,1-c][1,4]benzoxazin-3-one, 9-(1,1-dimethylethyl)-1-hydroxymethyl-5H-pyrimido[2,1][1,4]benzoxazin-3-one, and 9-chloro-1-hydroxymethyl-5H-pyrimido[2,1-c][1,4] benzoxazin-3-one.

EXAMPLE 6

9-Chloro-5H-pyrimido[2,1-c][1,4] benzoxazin-3-one (I;R$^1$=H, R$^2$=Cl and R$^3$=H)

An ethanol (150 ml) solution of 3-amino-6-chloro-2H-1,4-benzoxazine (9.0 g, 50 mmoles, described in Example 3) was warmed in the presence of ethyl propiolate (5.0 g, 51 mmoles) and then stirred at 20°–24° C. for 24 hr. The resulting brown precipitate was collected by filtration to give a brown solid (500 mg). The solid was triturated, with a mixture of benzene and hexane. The mother liquor from the filtration was heated at reflux for 30 minutes and then allowed to stand 2 days at 20°–24° C. The residue obtained upon removal of the solvent was recrystallized from benzene-methylene chloride-hexane. The residue was combined with the former precipitate and the mixtue was dissolved in methylene chloride. The organic solvent was subjected to several washings with dilute hydrochloric acid to ensure the removal of the contaminating amidine. The methylene chloride solution was dried and concentrated to give the title compound (2.25 g) as pale brown crystals; mp 222°–224° C. (after recrystallization from benzene-methylene chloride-hexane); IR(nujol)1695, 1640, 1598, 1548, 1500 cm$^{-1}$; NMR(DMSO-d$_6$) δ5.03(s,2H); 6.15–8.5 (m,5H); M+234; Anal. Calc'd; C, 56.30%; H, 3.01%; N, 11.94%; Found: C, 56.48%; H, 3.00%; N, 11.94%.

By following the procedure of Example 6, but replacing 3-amino-6-chloro-2H-1,4-benzoxazine with an equivalent amount of 3-amino-2H-1,4-benzoxazine, 3-amino-7-methyl-7-(1,1-dimethylethyl)-2H-1,4-benzoxazine, each described in Example 3, there is obtained, respectively:

5H-pyrimido[2,1-c][1,4] benzoxazin-3-one, 8-methyl-5H-pyrimido[2,1-c][1,4] -benzoxazin-3-one, and 9-(1,1-dimethylethyl)-5H-pyrimido[2,1-c][1,4] benzoxazin-3-one.

We claim:
1. A compound of formula I

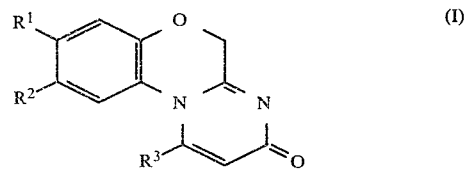

in which R$^1$ and R$^2$ are the same or different selected from the group of hydrogen, lower alkyl and halo; and R$^3$ is hydrogen, hydroxymethyl, or lower alkoxycarbonyl.

2. The compound of claim 1 in which R$^1$ is hydrogen or methyl, R$^2$ is hydrogen, tert-butyl or chloro and R$^3$ is hydrogen, hydroxymethyl or ethoxycarbonyl.

3. The compound of claim 1 in which R$^1$ is hydrogen or methyl, R$^2$ is hydrogen or chloro and R$^3$ is ethoxycarbonyl.

4. 3-Oxo-5H-pyrimido[2,1-c][1,4] benzoxazine-1-carboxylic acid, ethyl ester, as claimed in claim 1.

5. 8-Methyl-3-oxo-5H-pyrimido[2,1-c][1,4] benzoxazine-1-carboxylic acid, ethyl ester, as claimed in claim 1.

6. 9-(1,1-Dimethylethyl)-3-oxo-5H-pyrimido[2,1-c][1,4] benzoxazine-1-carboxylic acid, ethyl ester, as claimed in claim 1.

7. 9-Chloro-3-oxo-5H-pyrimido[2,1-c][1,4] benzoxazine-1-carboxylic acid, ethyl ester, as claimed in claim 1.

8. 1-Hydroxymethyl-5H-pyrimido[2,1-c][1,4] benzoxazine-3-one, as claimed in claim 1.

9. 9-Chloro-5H-pyrimido[2,1-c][1,4] benzoxazin-3-one, as claimed in claim 1.

10. A process for preparing the compound of claim 1 which comprises reacting a compound of formula II

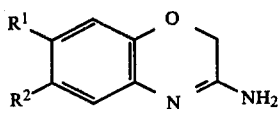 (II)

in which $R^1$ and $R^2$ are in the same or different selected from the group of hydrogen, lower alkyl and halo with a compound of formula $R^3C\equiv C-COO-$(lower alkyl)in which $R^3$ is hydrogen, hydroxymethyl or lower alkoxycarbonyl.

11. A method of preventing or treating anaphylactic reactions or allergic conditions in a mammal, which comprises administering to said mammal an effective anaphylactic alleviating or allergic alleviating amount of a compound according to claim 1.

12. A pharmaceutical composition for preventing or treating anaphylactic or allergic conditions, which comprises an anti-anaphylactic or anti-allergic effective amount of a compound according to claim 1, and a pharmaceutically acceptable carrier.

* * * * *